(12) United States Patent
Grey et al.

(10) Patent No.: US 7,194,895 B2
(45) Date of Patent: Mar. 27, 2007

(54) RHEOMETER

(75) Inventors: Ronald Garwood Grey, Beaumaris (AU); Geoffrey Mark Condick, Langwarrin (AU); Dean Svendsen, Endeavour Hills (AU)

(73) Assignee: GBC Scientific Equipment Pty Ltd, Victoria (AU)

( * ) Notice: Subject to any disclaimer, the term of this patent is extended or adjusted under 35 U.S.C. 154(b) by 0 days.

(21) Appl. No.: 10/523,917

(22) PCT Filed: Aug. 8, 2003

(86) PCT No.: PCT/AU03/01005
§ 371 (c)(1),
(2), (4) Date: Feb. 7, 2005

(87) PCT Pub. No.: WO2004/017048
PCT Pub. Date: Feb. 26, 2004

(65) Prior Publication Data
US 2005/0247115 A1 Nov. 10, 2005

(30) Foreign Application Priority Data
Aug. 16, 2002 (AU) .............................. 2002950831

(51) Int. Cl.
*G01N 11/10* (2006.01)
(52) U.S. Cl. ..................................... 73/54.23
(58) Field of Classification Search ............... 73/54.23, 73/54.24, 54.25, 54.26, 54.27
See application file for complete search history.

(56) References Cited

U.S. PATENT DOCUMENTS

| 3,933,032 A | 1/1976 | Tschoegl |
| 5,750,884 A * | 5/1998 | Field .......................... 73/54.24 |
| 2002/0178795 A1* | 12/2002 | Isogai et al. ............... 73/54.23 |

FOREIGN PATENT DOCUMENTS

| FR | 2 806 804 | 9/2001 |
| WO | WO 90/08309 | 7/1990 |
| WO | WO 02/086462 | 10/2002 |

* cited by examiner

*Primary Examiner*—Hezron Williams
*Assistant Examiner*—Paul M. West
(74) *Attorney, Agent, or Firm*—The Webb Law Firm

(57) ABSTRACT

A rheometer and method of making rheological measurements is disclosed, in which a sample is supported between plates and an alternating movement is applied by a driver, support rod and plate. Force and displacement measurements are taken and the property determined from those measurements. The vibrating signal which is applied is in the form of a frequency sweep signal having a monotonic group delay function. The top plate is provided with a surface which causes a meniscus to form up a side edge of the plate to reduce the spring nature of the sample when the movement is supplied to the sample, and a supporting rod which supports the top plate is preferably formed from a material having a low coefficient of thermal expansion so that the gap between the plates is maintained substantially constant if the sample is heated to take measurements at different temperatures.

22 Claims, 3 Drawing Sheets

RHEOMETER

FIELD OF THE INVENTION

This invention relates to a rheometer and, in particular, to a rheometer which can measure the complex viscosity and complex modulus of small volumes of fluids, as well as other rheological properties of materials such as elasticity.

BACKGROUND ART

Most conventional rheometers which measure viscosity, often simply referred to as viscometers, cannot be used for measuring viscosities of non-Newtonian samples. Furthermore, most conventional viscometers need large amounts of sample in order to enable measurements to be made. This is therefore a significant disadvantage, because in many cases, only very small amounts of sample are available for analysis.

SUMMARY OF THE INVENTION

The object of the present invention is to provide a rheometer which can provide measurements with only small amounts of sample and which can also make accurate measurements.

The invention provides a rheometer for determining a rheological property of a sample, comprising:
- a driver for applying an alternating movement to a surface of the sample for causing an alternating movement of the sample;
- a force measuring device for providing a force signal indicative of the reaction force exerted by the sample on the driver;
- a displacement measuring device for providing a signal indicative of the alternating movement of the sample;
- a processor for receiving the force signal and the movement signal to determine the rheological property of the sample; and
- a signal generator for supplying to the driver a frequency sweep signal having a monotonic group delay function to cause the driver to supply the alternating movement of the sample.

Thus, this aspect of the invention enables very small amounts of sample to be used to enable measurements to take place, and also the generating means ensures that harmonics from non-linearities (ie. distortion) are distributed in a well-defined way, rather than randomly across the frequency spectrum, which can be corrected for in the data processing by the processing means. Furthermore, the effect of intermittent external noise sources is confined to the frequencies during which they occurred, rather than being spread across the whole spectrum. Thus, the nature of the signal applied to the vibrating means which creates the reaction force, and therefore produces the force signal and the movement signal, enables better processing and therefore more accurate results to be obtained.

Preferably, the frequency sweep signal has a monotonic group delay function with a maximum value less than the acquisition period.

Preferably the frequency sweep signal has small crest factors and most preferably, close to 3 dB if using a flat amplitude envelope in the time domain. This provides the best practical crest factor and so gives the highest signal to noise ratio in terms of analogue to digital resolution and noise generated by the sampling electronics. The frequency sweep function also provides the ability to prescribe the amplitude envelope in the time domain and thus gives the rheologist control of this parameter. This in turn enables the maximum strain rates to be constrained to within the linear region of the sample.

The frequency sweep signal also enables fading of the start and end points to zero amplitude, which means that there are no unexpected transitions in the signal being injected into the sample, and so the sample integrity is preserved.

This form of signal also provides the ability to prescribe the spectral content envelope in the frequency domain, such as flat linear and log envelopes. This enables the rheologist to control how much energy is put into the sample at different frequencies. It also enables the signal to noise ratio of the stress measurement to be equalised, since typical samples do not have a flat transfer function.

Preferably the driver includes a driver having terfenite material and means for supplying an electromagnetic force to the terfenite material to produce the alternating movement.

Preferably the apparatus includes a sample support comprised of a top plate and a bottom plate which define a space for receiving the sample.

Preferably the displacement measuring device comprises a displacement transducer.

Preferably the force measuring device comprises a load cell.

Preferably the processor includes an analogue to digital converter for converting the signal from the load cell to a digital signal, and an analogue to digital converter for converting the signal from the displacement measuring means to a digital signal.

Preferably the processor is for determining the fourier transform of both the force signal and the movement signal, and the ratio of the fourier transform of the force signal $F(\omega)$ to the fourier transform of the movement signal $H(\omega)$.

Preferably at least one of the top plate and bottom plate is circular and has a radius a and the plates are separated by an average distance h and the property which is calculated is the complex modulus $$G^*(\omega) = h^3/3\pi a^4 \times F(\omega)/H(\omega).$$

Preferably the signal generator is for supplying the frequency sweep signal which is ramped up at commencement of the signal and ramped down at cessation of the signal.

Preferably the signal is ramped up to full scale by a ramp function given by $\sin^2(\pi \times i/2n)$ and ramped down by a ramp function given by $\cos^2(\pi \times i/2n)$ where there are n items in the signal and i indexes a particular item.

Preferably the ramping up of the signal and ramping down of the signal is performed by multiplying the signal for one signal period to respectively grow the signal from zero and then to attenuate the signal back to zero.

The invention also provides a method of determining a rheological property of a sample, comprising:
- applying by a driver an alternating movement to a surface of the sample for causing an alternating movement of the sample;
- measuring a force signal indicative of a reaction force exerted by the sample;
- measuring a signal indicative of the alternating movement of the sample;
- processing the force signal and the movement signal to determine the rheological property of the sample; and
- supplying to the driver a frequency sweep signal having a monotonic group delay function to produce the alternating movement of the sample.

Preferably, the frequency sweep signal has a monotonic group delay function with a maximum value less than the acquisition period.

Preferably the frequency sweep signal has small crest factors and most preferably, close to 3 dB if using a flat amplitude envelope in the time domain.

Preferably the vibrating means includes a driver including terfenite material and means for supplying an electromagnetic force to the terfenite to produce the alternating movement.

Preferably the method includes supporting the sample between a top plate and a bottom plate which define a space for receiving the sample.

Preferably the displacement is measured by a displacement transducer.

Preferably the force is measured by a load cell.

Preferably the processing includes converting the force signal to a digital signal, and converting the displacement signal to a digital signal.

Preferably the processor further includes determining the fourier transform of both the force signal and the movement signal, and the ratio of the fourier transform of the force signal to the fourier transform of the movement signal.

Preferably at least one of the top plate and bottom plate is circular and has a radius a and the plates are separated by an average distance h and the property which is calculated is the complex modulus $$G^*(\omega) = h^3/3\pi a^4 \times F(\omega)/H(\omega).$$

Preferably the frequency sweep signal which is ramped up at commencement of the signal and ramped down at cessation of the signal.

Preferably the signal is ramped up to full scale by a ramp function given by $\sin^2(\pi \times i/2n)$ and ramped down by a ramp function given by $\cos^2(\pi \times i/2n)$ where there are n items in the signal and i indexes a particular item.

Preferably the ramping up of the signal and ramping down of the signal is performed by multiplying the signal for one signal period to respectively grow the signal from zero and then to attenuate the signal back to zero.

A further aspect of the invention is concerned with problems which are created when a fluid sample is located between the top plate and the bottom plate of the rheometer. If the sample is in the form of a fluid, the meniscus of the fluid can effectively form a spring between the top and bottom plates. That is, when the alternating force is applied to the sample, the meniscus effectively provides a resistance or load against that force, and this in turn causes errors in the resulting measurements.

Thus, the invention also provides a rheometer for determining a rheological property of a fluid sample, comprising:
  a driver for applying an alternating movement to a surface of the sample for causing an alternating movement of the sample;
  force measuring device for providing a force signal indicative of the reaction force exerted by the sample on the driver;
  displacement measuring device for providing a signal indicative of the alternating movement of the sample;
  processor for receiving the force signal and the movement signal to determine the rheological property of the sample; and
  sample support having a top plate and a bottom plate between which a space is provided for receiving the sample, one of said plates being moveable relative to the other plate by the vibrating means, said one of said plates having a side edge, means for causing the fluid sample to extend up the side wall of the said one of the plates to form a concave meniscus so that upon movement of the said one of the plates, the meniscus will slip on the edge of the top plate thereby reducing the spring nature of the meniscus to reduce errors in the resulting measurement due to the spring nature of the meniscus.

Preferably the said support comprises a quartz surface on the at least said one plate at least in the vicinity of the meniscus so that the fluid flows up the said side surface thereby creating the meniscus which extends up the side surface of the said one plate.

Preferably the said at least one plate is formed from steel and the quartz surface is formed by vacuum depositing quartz onto the said steel plate.

Preferably the quartz surface has a thickness of about 100 micrometers.

Preferably both the top plate and the bottom plate are provided with the quartz surface having the thickness of about 100 micrometers.

This embodiment, in relation to aqueous fluids, lowers the contact angle of the meniscus with the said one plate and allows the fluid sample to thereby be used with steel plates. This in turn allows relatively cheap plates to be used and also plates which are easy to clean and less porous than plain hardened stainless steel plates.

Preferably the said one of the plates comprises the top plate.

The invention also provides a method of determining a rheological property of a sample fluid, comprising:
  applying an alternating movement to a surface of the sample for causing an alternating movement of the sample;
  measuring a force signal indicative of the reaction force exerted by the sample on the vibrating means;
  measuring a signal indicative of the alternating movement of the sample;
  processing the force signal and the movement signal to determine the rheological property of the sample; and
  supporting the sample between a top plate and a bottom plate between which a space is provided for receiving the sample fluid, one of said plates being moveable relative to the other plate by the vibrating means, said one of said plates having a side edge, and causing the sample fluid to extend up the side wall of the said one of the plates to form a concave meniscus so that upon movement of the said one of the plates, the meniscus will slip on the edge of the top plate thereby reducing the spring nature of the meniscus to reduce errors in the resulting measurement due to the spring nature of the meniscus.

Preferably the step of causing the sample fluid to extend up the side wall comprises providing said one plate with a quartz surface at least in the vicinity of the meniscus so that the fluid flows up the said side surface thereby creating the meniscus which extends up the side surface of the said one plate.

Preferably the providing step comprises vacuum depositing quartz onto the said one plate.

Preferably the quartz surface has a thickness of about 100 micrometers.

Preferably both the top plate and the bottom plate are provided with the quartz surface having the thickness of about 100 micrometers.

Preferably the said one of the plates comprises the top plate.

A further aspect of the invention is concerned with determining rheological properties of a sample at different temperatures. In order to provide rheological information, it is often necessary to consider the properties of a sample at different temperatures, and therefore in accordance with this aspect of the invention, the method and apparatus needs to cater for this possibility.

The invention may therefore be said to reside in a method of determining a rheological property of a sample, comprising:
- supporting the sample between a pair of support plates spaced apart by a predetermined distance;
- applying an alternating movement to one of the support members to cause an alternating movement of the sample;
- measuring a force signal indicative of a reaction force exerted by the sample;
- measuring a signal indicative of the alternating movement of the sample;
- processing the force signal and the movement signal to determine the rheological property of the sample;
- controlling the temperature of the sample so that the rheological property can be determined at different sample temperatures; and
- maintaining the distance between the support member substantially constant notwithstanding the change in temperature of the sample.

By maintaining the distance between the support member, the temperature change of the sample does not influence the distance between the members which would in turn influence the measurement of the rheological property, and therefore accurate measurements can be obtained at different temperatures.

Preferably the alternating movement is supplied by a driver and the method includes supplying to the driver a frequency sweep signal having a monotonic group delay function to produce the alternating movement of the sample.

Preferably the driver is connected to one of the support members by a connecting member and the distance between the support member is maintained substantially constant by forming the connecting member from a material having low coefficient of thermal expansion.

Most preferably the connecting member is formed from metal sold under the trade name INVAR and preferably the support member is gold plated.

The invention also provides a rheometer for determining a rheological property of a sample, comprising:
- a pair of support members for supporting the sample therebetween, the support member being spaced apart by a predetermined distance when making measurements;
- a connecting member connected to one of the support members;
- a driver for applying an alternating movement to the connecting member and the said one of the support member so the movement is applied to a surface of the sample for causing an alternating movement of the sample;
- force measuring device for providing a force signal indicative of the reaction force exerted by the sample of the driver;
- displacement measuring device for providing a signal indicative of the alternating movement of the sample;
- a processor for receiving the force signal and the movement signal to determine the rheological property of the sample;
- a temperature controller for controlling the temperature of the sample; and
- wherein the connecting member is formed from a material having a low coefficient of thermal expansion so that the change in temperature caused by the temperature control means does not alter the space between the support members.

Preferably the connecting member comprises a support rod.

Preferably the support members are plates and in some embodiments the support rod and the plates are formed from the material having low thermal coefficient of expansion.

Preferably the temperature controller is a peltier heater. However, in other embodiments a recycling fluid type heater or a resistive heater could be used.

A further disadvantage of conventional rheometers is the possibility of damaging the sample because of the nature of the sweep signal which is applied to the driver. We have found that a sudden output transition (either in terms of instantaneous displacement or velocity change) possibly associated with the onset of a displacement waveform, could unduly disturb the structure of a delicate sample. Thus, if the signal which is applied to the driver does not have a well behaved start and end trajectory, the possibility of damage to the sample does exist. In other words, sudden starting and stopping an arbitrary displacement wave could inadvertently inject high frequency and/or amplitude displacement waves through the sample, which could damage structures of interest. This may make the sample under tests behave differently than expected. Given that the signals applied to the driver are periodic in nature, once a function has started, this problem will not effect immediate repetitions of the function. However, as noted above, it will effect cessation of the function or the instantaneous onset of a different function.

Thus, the invention further provides a rheometer for determining a rheological property of a sample, comprising:
- a driver for applying an alternating movement to a surface of the sample for causing an alternating movement of the sample;
- a force measuring device for providing a force signal indicative of the reaction force exerted by the sample on the driver;
- a displacement measuring device for providing a signal indicative of the alternating movement of the sample;
- a processor for receiving the force signal and the movement signal to determine the rheological property of the sample; and
- a signal generator for supplying to the driver a signal to cause the driver to apply the alternating movement to the surface of the sample, which signal is ramped up at commencement of the signal and ramped down at cessation of the signal to prevent arbitrary displacements of the sample which could damage structures of interest in the sample.

Preferably the signal is ramped up to full scale by a ramp function given by $\sin^2(\pi \times i/2n)$ and ramped down by a ramp function given by $\cos^2(\pi \times i/2n)$ where there are n items in the signal and i indexes a particular item.

Preferably the signal is a frequency sweep signal having a monotonic group delay function.

The invention also provides a method of determining a rheological property of a sample, comprising:
- applying by a driver an alternating movement to a surface of the sample for causing an alternating movement of the sample;
- measuring a force signal indicative of a reaction force exerted by the sample;

measuring a signal indicative of the alternating movement of the sample;

processing the force signal and the movement signal to determine the rheological property of the sample; and supplying to the driver a signal which is ramped up at commencement of the signal and ramped down at cessation of the signal to prevent arbitrary displacements of the sample that could inadvertently damage structures of interest in the sample.

Preferably the signal is ramped up to full scale by a ramp function given by $\sin^2(\pi x i/2n)$ and ramped down by a ramp function given by $\cos^2(\pi x i/2n)$ where there are n items in the signal and i indexes a particular item.

Preferably the signal is a frequency sweep signal having a monotonic group delay function to produce the alternating movement of the sample.

BRIEF DESCRIPTION OF THE DRAWINGS

A preferred embodiment of the invention will be described, by way of example, with reference to the accompanying drawings, in which.

DETAILED DESCRIPTION OF THE PREFERRED EMBODIMENT

Figure 1:
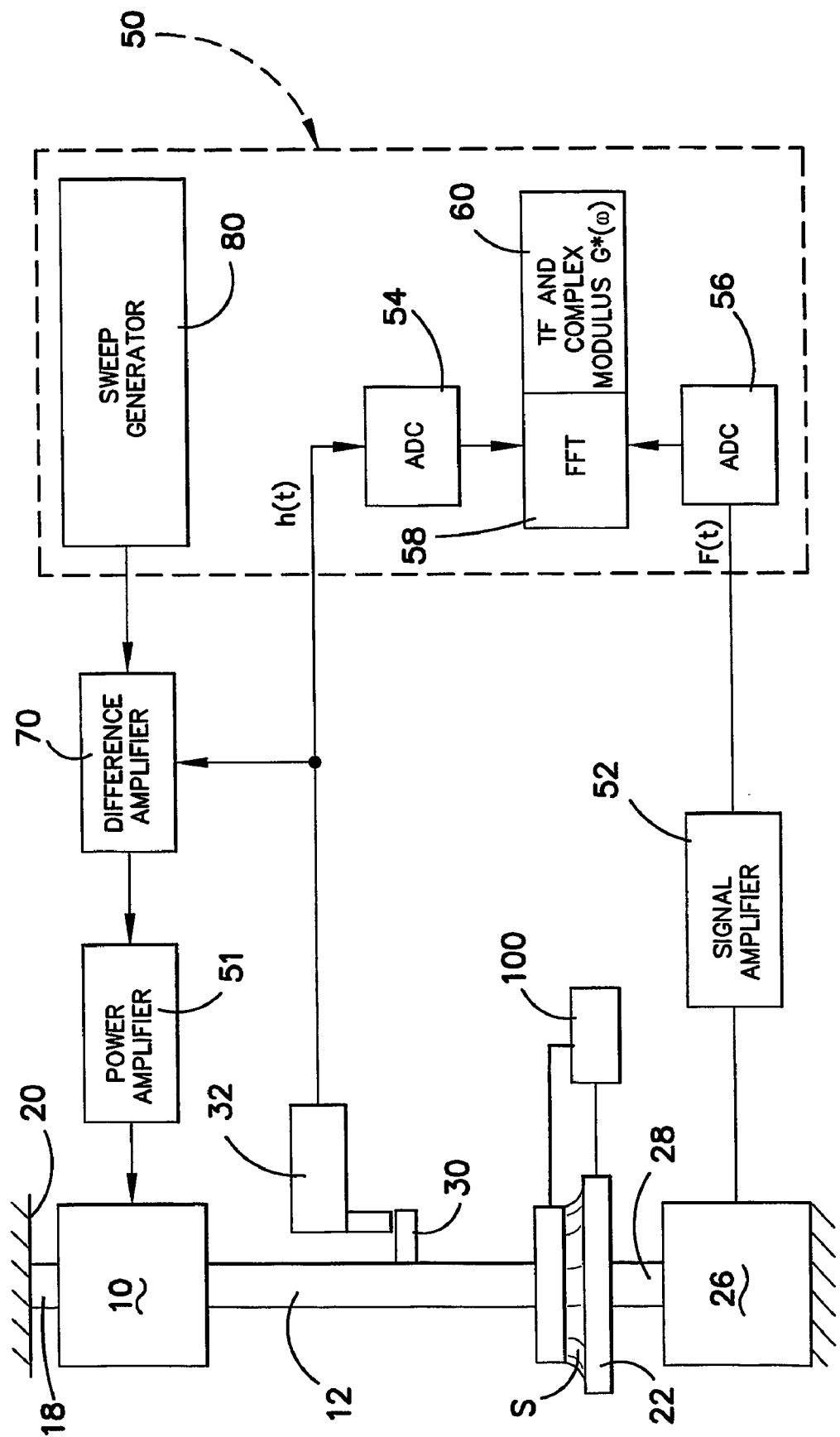
FIG. 1 is a block diagram of a rheometer according to the preferred embodiment.

With reference to FIG. 1, a rheometer according to the preferred embodiment of the invention is shown which has a driver 10 which is preferably formed from a terfenite material and electromagnets for supplying a magnetic field to the terfenite material. Most preferably the terfenite material is in the form of rods which, when the magnetic field is applied, grow in the magnetic field. Thus, by applying an alternating magnetic field to the terfenite rods, the movement of the terfenite rods causes a vibration which creates an alternating movement of the driver 10. Such drivers are known per se and therefore need not be defined in further detail.

The driver 10 has a connecting rod 12 formed from metal which can vibrate with the driver 10, and the rod 12 is connected to top plate 14 of a sample support station 16. The driver 10 may be supported by support 18 to a casing 20 or housing of the rheometer.

The sample station 16 includes a bottom plate 22 and a space 24 is provided between the top plate 14 and the bottom plate 22 in which a sample S can be located. The bottom plate 22 is connected to a load cell 26 by a rod 28.

The top plate 14 and bottom plate 22 are preferably circular, and the top plate has a diameter a which is smaller than the bottom plate 22.

The connecting rod 12 has an abutment 30 which moves with the connecting rod 12 and a displacement transducer 32 is associated with the abutment 30 for measuring the displacement of the abutment 30 and therefore the displacement or vibration of the driver 10 and sample 12, and therefore also of the top plate 14.

Thus, the displacement transducer 32 produces a displacement signal h(t) which is indicative of the alternating movement of the top plate 14 as driven by the driver 10.

The load cell 26 produces a force signal F(t) which is indicative of the force supplied by the sample S to the bottom plate 22 upon vibrating movement of the top plate 14.

The displacement signal h(t) and the force signal F(t) are provided to processor 50. The force signal F(t) may be amplified by amplifier 52 before application to the processor 50. The processor 50 includes an analogue to digital converter 54 for converting the signal h(t) into a digital signal, and an analogue to digital converter 56 for converting the signal F(t) to a digital signal. The digital signals from the converters 54 and 56 are provided to a processing section 58 which determines the fourier transform of the signal h(t) which is expressed H($\omega$) and the fourier transform of the signal F(t) which is expressed as F($\omega$). The processor 58 also determines the ratio of the fourier transforms F($\omega$)/H($\omega$).

The processor 50 also includes a processing section 60 for determining the complex modulus G*($\omega$) of the sample which is given by the equation:

$$G^*(\omega) = h^3/3\pi a^4 \times F(\omega)/H(\omega)$$

In the preferred embodiment of the invention the displacement signal h(t) is also fed back to differential amplifier 70 and the differential amplifier also receives a frequency sweep signal from signal generator 80. The differential amplifier 70 outputs the difference of the signals h(t) and the sweep signal from the generator 80 to power amplifier 51 and then to the driver 10 so as to actuate the driver 10 and drive the driver 10 to produce the vibrating or alternating movement of the driver 10 which is imparted to the plate 14.

Figure 2:
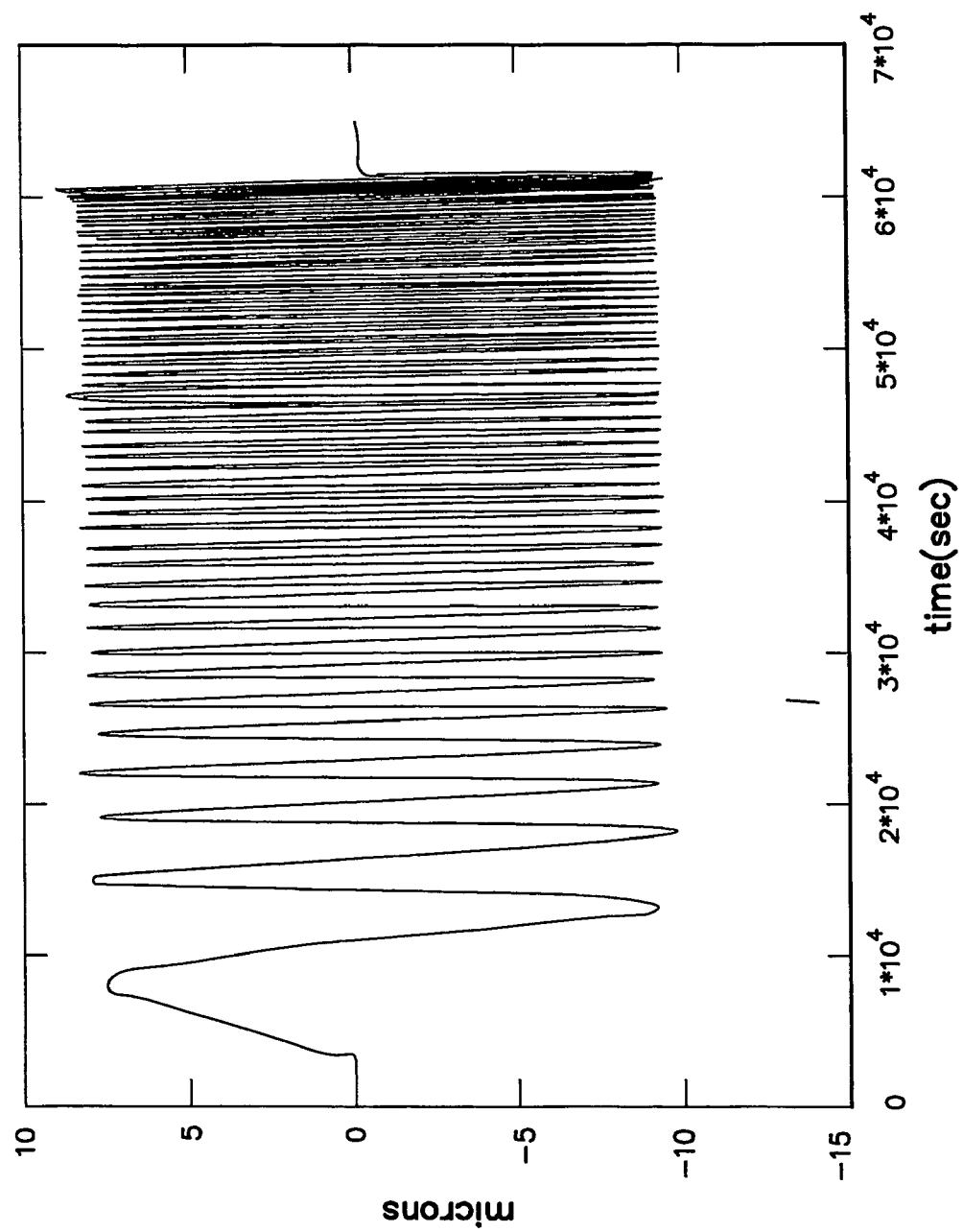
FIG. 2 is a graph showing the sweep function of the preferred embodiment.

FIG. 2 is a representative trace of the frequency sweep signal which is supplied by the generator 80 to the driver 10. The signal supplied by the generator 80 is a frequency sweep or chirp function which has a monotonic group delay function with a maximum value less than the acquisition period. Thus, the harmonics from non-linearities (ie. distortions) are distributed in a well-defined way rather than randomly across the frequency spectrum, and therefore can be corrected for in the data processing within the processor 50 so as to improve the measurement results of the complex viscosity of the sample S. This form of signal applied to the driver 10 also results in the effect of intermittent external noise sources being confined to the frequencies during which they occur, rather than being spread across the entire spectrum of the signal.

This form of signal also enables small crest factors (close to 3 dB if using a flat amplitude envelope in the time domain). This is about the best practical crest factor which can be obtained, and is therefore only 3 decibels above the theoretical best case, which cannot be achieved because of bandwidth limits. Thus, this gives the highest signal to noise ratio in terms of A/D resolution and noise generated by the sampling electronics of the displacement transducer 32 and the load cell 26.

This form of signal also provides the ability to prescribe the amplitude envelope in the time domain, and therefore enables the maximum strain rates to be constrained to within the linear region of the sample S. Furthermore, fading of the start and end points to zero amplitude is also possible, and this results in no unexpected transitions in the signal being injected into the sample, and so the sample integrity is preserved. This form of signal also provides the ability to prescribe the spectral content envelope in the frequency domain, such as flat, linear and log envelopes. This enables the rheologist to control how much energy is input into the sample at different frequencies, and also enables a signal to noise ratio of the stress measurement to be equalised, since typical samples do not have a flat transfer function.

Thus, the use of the generator 80 which produces the sweep function described above therefore provides more accurate results and better control over the analysis of samples in order to determine the complex viscosity of the sample.

Whilst the generator 80 preferably supplies the type of signal referred to above, the generator is also capable of delivering many types of displacement signals to cause the alternating movement of the sample. In some environments, other signals may be useful or desirable in some environments. We have found that if the nature of the signal is such that sudden transitions in terms of instantaneous displacement or velocity change are created, delicate structures in the sample could be damaged. Because the nature of signals generally applied are periodic, the time at which these types of displacements are likely to occur is when the signal initially commences and when the signal ceases. Once the signal has started, immediate repetitions of the function do not create any problem.

In accordance with one embodiment of the invention, the signal is therefore ramped up at commencement and ramped down at cessation so as to avoid displacements which could damage the sample. Most preferably the signal is slowly ramped up from zero to full scale over the course of one full signal period, and is ramped down in the same way over the course of one full function period. The signal is ramped up and ramped down by ramp functions given by $\sin^2(\pi x i/2n)$ and $\cos^2(\pi x i/2n)$ respectively, where there are n items in the given signal or function which represents the signal, and i indexes a particular item. Thus, these ramp functions are multiplied by the desired signal for one signal period to respectively grow the function from zero and when it is desired to stop the signal, to attenuate the signal back to zero. Additionally, these signals can be used to transition different displacement functions which may be applied to the sample in one measurement. Thus, whilst one signal is ramping down, another can be ramping up, and they can be combined by addition as follows:

signal 1×ramp down+signal 2×ramp up

Whilst the signal described with reference to FIG. 1 behaves relatively well, it can also be ramped up and ramped down in the manner described above to further improve the nature of the signal which is applied to the driver to move the sample, and therefore further ensure that the nature of the movement is unlikely to damage delicate structures in the sample which may be of interest, and which may contribute to the measurements which are made.

Figure 3:
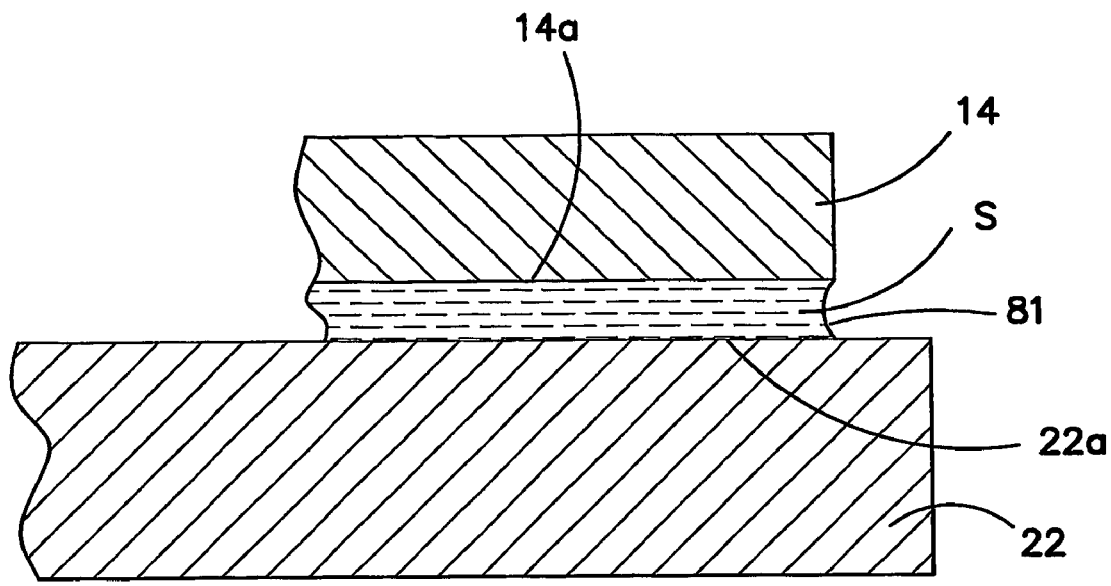
FIG. 3 is an enlarged view of the plates of a rheometer according to the prior art.

FIG. 3 is a diagram of the sample station 16 in which the top plates 14 and 22 of a prior art system is shown. Typically the plates 14 and 22 are formed from stainless steel and the sample S which is constrained between the plates 14 and 22 forms a meniscus 81 which extends from the lower surface 14a of the top plate to the upper surface 22a of the bottom plate. This meniscus 81 effectively acts like a spring which provides a resistance to the vibrating movement which is imparted to the sample S by the top plate 14. This is because the meniscus 81 is constrained between the surfaces 14a and 22a and therefore must be compressed and decompressed as the plate 14a moves. This tendency of the meniscus to act like a spring therefore tends to alter the nature of the alternating flow of the sample fluid S which is created, thereby introducing errors into the measurements which are obtained.

Figure 4:
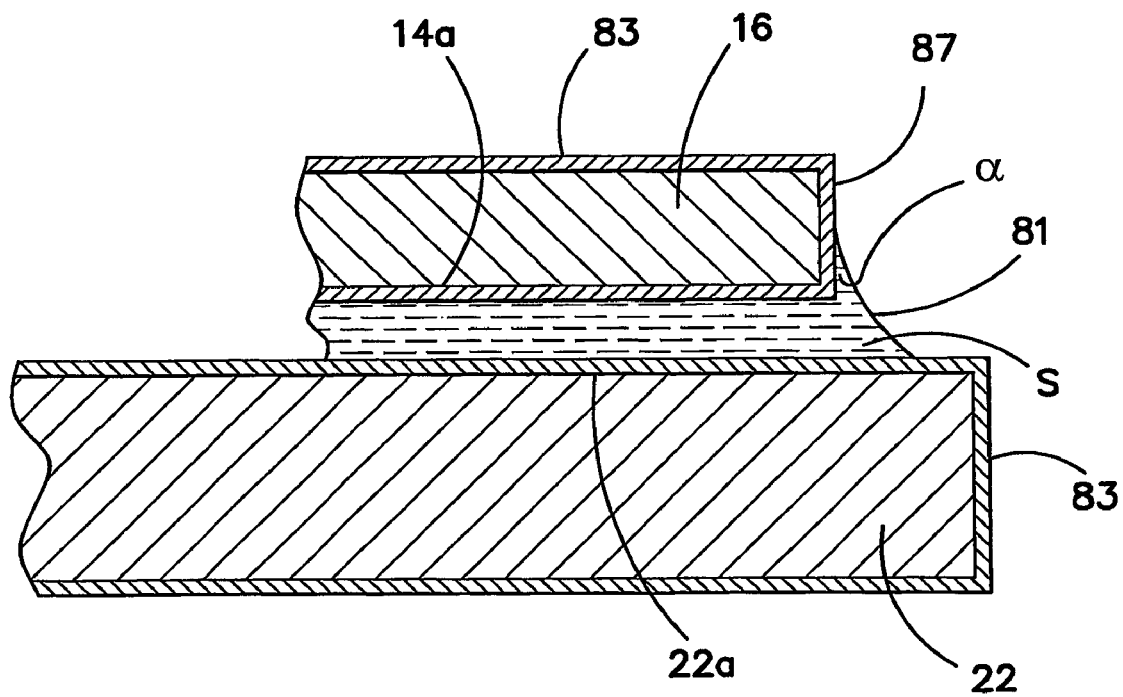
FIG. 4 is a view similar to FIG. 3, but of the preferred embodiment of the present invention.

The preferred embodiment of the invention overcomes this problem by providing the plates 16 and 22 with a surface which is formed from quartz, as shown by the surface layer 83 provided on the plates 16 and 22. The surface layer 83 is preferably formed from vacuum deposition and is about 100 micrometers thick. The result of forming the quartz layer is that the meniscus 81, as shown in FIG. 4, is not constrained between the surfaces 14a and 22a, but will tend to creep up the side edge 87 of the plate 16. In other words, the sample S overfills the space between the plates 16 and 22, and the meniscus 81 will slip on the side edge 87 as the plate 16 vibrates. Thus, the springing action is not produced which would cause a slight resistance to the fluid flow of the material and, according to the preferred embodiment, results are therefore improved.

The plates 16 and 22 are still formed from stainless steel but are provided with the quartz layer 83 and therefore this provides a relatively cheap sample station S, and therefore plates which are easy to clean and less porous than plain hardened stainless steel.

The meniscus 81 forms a concave shape as shown in FIG. 4, and therefore a very small contact angle α between the meniscus 81 and the side edge 87. However, the meniscus 81, as is shown in FIG. 5, may be concave.

By coating the plates 16 and 22 with the quartz layer 83, the aqueous samples S will therefore take up a very small contact angle, and therefore the configuration or shape as shown in FIG. 4, which will not exhibit the spring nature of the meniscus and allow good slippage between the plate 16 and the fluid S. Thus, the nature of the flow of the material caused by the vibrating movement of the plate 16 is not impaired by the meniscus and therefore the signals h(t) and F(t) are more indicative of the actual nature of the sample and therefore much more accurate results are obtained.

In some instances, it is desirable to determine the rheological properties of the sample S at different temperatures. In order to enable this to happen, a temperature controller 100 is used to heat the sample S so measurements can be made at different temperatures. The heater 100 is most preferably a Peltiar heater. However, other forms of temperature controller such as recycling fluid type controllers or resistive heaters could be used. Recycling fluid type controllers have particular application if it is desired to cool the temperature of the sample S below ambient temperature.

If the sample temperature is changed, the change in temperature can be conducted through to the support plate 14 and support rod 12. Because the support rod 12 is relatively elongate, it may expand or contract due to the change in temperature, which in turn will change the gap or space between the plate 22 and the plate 14 which will effect the accuracy of measurements which are made at the different temperatures. In order to ensure that the space between the plates 14 and 22 is maintained substantially constant, the support rod 12 is most preferably formed from a material having low coefficient of thermal expansion. Most preferably, the rod 12 is formed from a metal sold under the name Invar, and most preferably the rod 12 is gold plated. Because most of the thermal expansion is likely to take place in the elongate rod 12, it is not necessary that the top plate 14 or bottom plate 22 be formed from material having low coefficient of thermal expansion. However, if desired, these plates could also be formed from the same material as the rod 12.

In this embodiment of the invention, because the top plate 14 undergoes generally vertical movement, the top plate 14 can also be heated as well as the bottom plate 14. Heating is performed by the same type of heaters as referred to above. FIG. 1 schematically shows a single heater heating both the top plate and the bottom plate. However, two separate heaters would be used to heat both the top plate and the bottom plate.

In the claims which follow and in the preceding description of the invention, except where the context requires otherwise due to express language or necessary implication, the word "comprise", or variations such as "comprises" or "comprising", is used in an inclusive sense, ie. to specify the presence of the stated features but not to preclude the presence or addition of further features in various embodiments of the invention.

Since modifications within the spirit and scope of the invention may readily be effected by persons skilled within the art, it is to be understood that this invention is not limited to the particular embodiment described by way of example hereinabove.

The invention claimed is:

1. A rheometer for determining a rheological property of a sample, comprising:
    a driver for applying an alternating movement to a surface of the sample for causing an alternating movement of the sample;
    a force measuring device for providing a force signal indicative of the reaction force exerted by the sample on the driver;
    a displacement measuring device for providing a signal indicative of the alternating movement of the sample;
    a processor for receiving the force signal and the movement signal to determine the rheological property of the sample; and
    a signal generator for supplying to the driver a frequency sweep signal having a monotonic group delay function to cause the driver to supply the alternating movement of the sample,
    wherein the frequency sweep signal has a monotonic group delay function with a maximum value less than the acquisition period.

2. The rheometer of claim 1 wherein the frequency sweep signal has small crest factors close to 3 dB if using a flat amplitude envelope in the time domain.

3. The rheometer of claim 1 wherein the apparatus includes a sample support comprised of a top plate and a bottom plate which define a space for receiving the sample.

4. The rheometer of claim 3 wherein at least one of the top plate and bottom plate is circular and has a radius a, the plates are separated by an average distance h, $F(\omega)$ is a force signal, $H(\omega)$ is a movement signal and the property which is calculated is the complex modulus $$G^*(\omega)=h^3/3\pi a^4 \times F(\omega)/H(\omega).$$

5. The rheometer of claim 1 wherein the displacement measuring device comprises a displacement transducer.

6. The rheometer of claim 1 wherein the force measuring device comprises a load cell.

7. The rheometer of claim 1 wherein the processor includes an analogue to digital converter for converting the signal from the load cell to a digital signal, and an analogue to digital converter for converting the signal from the displacement measuring means to a digital signal.

8. The rheometer of claim 7 wherein the processor is for determining the fourier transform of both the force signal and the movement signal, and the ratio of the fourier transform of the force signal $F(\omega)$ to the fourier transform of the movement signal $H(\omega)$.

9. The rheometer of claim 1 wherein the signal generator is for supplying the frequency sweep signal which is ramped up in amplitude at commencement of the signal and ramped down in amplitude at cessation of the signal.

10. The rheometer of claim 9 wherein the signal is ramped up to full scale by a ramp function given by $\sin^2(\pi x i/2n)$ and ramped down by a ramp function given by $\cos^2(\pi x i/2n)$ where there are n items in the signal and i indexes a particular item.

11. The rheometer of claim 10 wherein the ramping up of the signal and ramping down of the signal is performed for one signal period to respectively grow the signal from zero and then to attenuate the signal back to zero.

12. A method of determining a rheological property of a sample, comprising:
    applying by a driver an alternating movement to a surface of the sample for causing an alternating movement of the sample;
    measuring a force signal indicative of a reaction force exerted by the sample; measuring a signal indicative of the alternating movement of the sample;
    processing the force signal and the movement signal to determine the rheological property of the sample; and
    supplying to the driver a frequency sweep signal having a monotonic group delay function to produce the alternating movement of the sample,
    wherein the frequency sweep signal has a monotonic group delay function with a maximum value less than the acquisition period.

13. The method of claim 12 wherein the frequency sweep signal has small crest factors close to 3 dB if using a flat amplitude envelope in the time domain.

14. The method of claim 12 wherein the method includes supporting the sample between a top plate and a bottom plate which define a space for receiving the sample.

15. The method of claim 14 wherein at least one of the top plate and bottom plate is circular and has a radius a, the plates are separated by an average distance h, $F(\omega)$ is a force signal, $H(\omega)$ is a movement signal and the property which is calculated is the complex modulus $$G^*(\omega)=h^3/3\pi a^4 \times F(\omega)/H(\omega).$$

16. The method of claim 12 wherein the displacement is measured by a displacement transducer.

17. The method of claim 12 wherein the force is measured by a load cell.

18. The method of claim 12 wherein the processing includes converting the force signal to a digital signal, and converting the displacement signal to a digital signal.

19. The method of claim 12 wherein the processing further includes determining the fourier transform of both the force signal and the movement signal, and the ratio of the fourier transform of the force signal to the fourier transform of the movement signal.

20. The method of claim 12 wherein the frequency sweep signal which is ramped up in amplitude at commencement of the signal and ramped down in amplitude at cessation of the signal.

21. The method of claim 20 wherein the signal is ramped up to full scale by a ramp function given by $\sin^2(\pi x i/2n)$ and ramped down by a ramp function given by $\cos^2(\pi x i/2n)$ where there are n items in the signal and i indexes a particular item.

22. The method of claim 21 wherein the ramping up of the signal and ramping down of the signal is performed for one signal period to respectively grow the signal from zero and then to attenuate the signal back to zero.

* * * * *